(12) United States Patent
Rutherford et al.

(10) Patent No.: US 7,273,938 B2
(45) Date of Patent: Sep. 25, 2007

(54) PREPARATION OF NOVEL SUBSTITUTED HALOARENE COMPOUNDS

(75) Inventors: Jennifer L. Rutherford, Gales Ferry, CT (US); Joel M. Hawkins, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 1 day.

(21) Appl. No.: 11/180,850

(22) Filed: Jul. 13, 2005

(65) Prior Publication Data

US 2006/0030714 A1 Feb. 9, 2006

Related U.S. Application Data

(60) Provisional application No. 60/589,152, filed on Jul. 19, 2004.

(51) Int. Cl.
C07D 213/02 (2006.01)
C07D 213/04 (2006.01)
C07D 213/24 (2006.01)
C07D 213/28 (2006.01)
C07D 213/30 (2006.01)

(52) U.S. Cl. ............................. 546/345; 546/1; 546/26; 568/713

(58) Field of Classification Search ................ 546/345, 546/1; 547/26; 568/713
See application file for complete search history.

(56) References Cited

U.S. PATENT DOCUMENTS 6,420,565 B2 * 7/2002 O'Shea et al. ............... 546/345
2002/0016470 A1 2/2002 O'Shea et al.

FOREIGN PATENT DOCUMENTS

WO    WO 01/90072 A1    11/2001

OTHER PUBLICATIONS

X. Wang, et al., Tetrahedron Lett., vol. 41, Issue 22, p. 4335-4338 (2000).
W. Li, et al. J. Org. Chem., vol., 67, Issue 15, p. 5394-5397 (2002).
F. D. Therkelsen, et al., Org. Lett., vol., 6, Issue 8, p. 1991-1994 (2004).
H-G Schmalz, et al., Current Opinion in Drug Discovery & Development 2004, vol. 7, No. 6, p. 882-895.
David S. Ennis et al., Organic Process Research & Development 1998, vol. 2, p. 287-289.
Hans-Gunther Schmaiz, CHI Conference, :La Jolla, Feb. 25, 2004.
Hans-Gunther Schmaiz, CPC User Forum, Dec. 4, 2003.
Richard W. Draper, et al., Novel Stereoselective Syntheses of the Fused Benzazepine Dopamine D1 Antagonist (6aS, 13bR)-11-Chloro-6, 6a, 7, 8, 9, 13b-hexahydro-7-methyl-5H-benzo[d]lnaphth[2, 1-b]azepin-12-ol (Sch 39166): 2. L-Homophenylalanine-Based Syntheses, Organic Process Research & Development 1998, 2, pp. 186-193.

G. Evan Boswell, et al., Synthesis, Stereochemistry, and Opioid Receptor Binding Activity of Heterocyclic Analogues of BW373U86, Heterocyclic Chem.. 32, pp. 1801-1818 (1995).

* cited by examiner

Primary Examiner—Elvis O. Price
(74) Attorney, Agent, or Firm—Steve Zelson; Mary J. Hosley; James A. Jubinsky

(57) ABSTRACT

This invention relates to a new process for the preparation of novel substituted haloarene compounds of the formula I or IV:

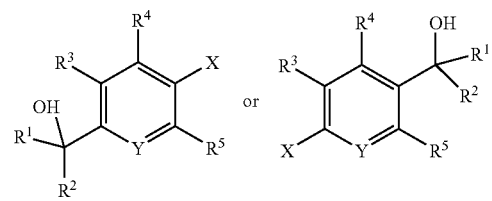

respectively, wherein $R^1$, $R^2$, $R^3$, $R^4$, $R^5$, X, and Y are as defined herein, that comprises a novel and efficient selective mono-lithiation of a dihaloarene of the formula II or V:

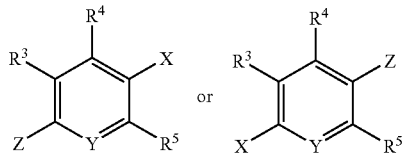

respectively, by an organo-lithium compound in the presence of a carbonyl reactant of the formula III:

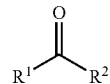

wherein $R^1$ and $R^2$ are as defined herein. In the process of the instant invention, the newly formed lithiated haloarene is sequentially quenched in situ by the carbonyl reactant to form said substituted haloarene. The process is suitable for batch or continuous flow systems. The substituted haloarenes produced by the process of the present invention are useful intermediates in the preparation of N-aryl or N-heteroaryl substituted pharmaceutically active compounds that include selective antagonists, inverse agonists and partial agonists of serotonin 1 ($5-HT_1$) receptors useful in treating or preventing depression, anxiety, obsessive compulsive disorder (OCD) and other disorders for which a $5-HT_1$ agonist or antagonist is indicated.

20 Claims, No Drawings

PREPARATION OF NOVEL SUBSTITUTED HALOARENE COMPOUNDS

The present application claims the benefit under 35 USC §119(e) of U.S. provisional application 60/589,152 filed Jul. 19, 2004.

BACKGROUND OF THE INVENTION

This invention relates to a new process for the preparation of novel substituted haloarene compounds that comprises a novel and efficient selective mono-lithiation of a dihaloarene by an organo-lithium compound in the presence of an enolizable carbonyl reactant. In the process of the instant invention the newly formed lithiated haloarene is immediately quenched in situ by the carbonyl reactant to form said substituted haloarene. The process of the instant invention operates at higher temperatures and higher concentrations and is more efficient than conventional methods in which the aryl lithium species is first formed and the carbonyl reactant is added in a subsequent step. High yields of the substituted haloarene are obtained in a practical one-step process since competitive addition of the organo-lithium compound to the carbonyl reactant and di-substitution of the arene occur only to a minor extent.

H.-G. Schmalz (CPC-User Forum, Frankfurt/Main, Germany, Dec. 3, 2003; Cambridge Healthtech Institute, Eleventh Annual Advancing Library Design and Organic Synthesis, La Jolla, Calif., Feb. 25, 2004) has described an in situ quench (ISQ) protocol wherein n-butyllithium is added to a preformed mixture of bromoarene and ketone under both batch and flow conditions. This protocol requires sterically hindered, non-enolizable ketones or the use of tertiary-butyllithium and cryogenic temperatures (−78° C.) for enolizable substrates.

US Published Application No. 20020016470A1; and X. Wang, et al., Tetrahedron Lett., 41:4335 (2000), describe reactions of 2,5-dibromopyridine with n-butyllithium which selectively lithiate in the 2-position if the solvent is toluene and in the 5-position if the solvent is tetrahydrofuran. The lithiation and quench are carried out sequentially at temperatures of −50° C. to −78° C. The concentration of the substrate in solution is 0.085M–0.28M, although at 0.28M the reagents and products are not entirely soluble.

W. Li, et al. J. Org. Chem., 67:5394(2002), describe an n-butyllithium in situ quench protocol for the preparation of arylboronic acids from the reaction of substrates such as 3-bromopyridine with borates (borates are non-enolizable).

F. D. Therkelsen, et al., Org. Lett., 6:1991(2004), details Barbier-type protocols (in situ quench) for the metallation of 4-halopyrimidines and in situ quench with electrophiles such as aldehydes. The metallation agents used were either magnesium ate complexes or butyllithium. The magnesium "ate" complexes worked effectively at both low (−76° C.) temperatures and 0° C. However, with n-butyllithium, the reaction only worked at −76° C. and no desired product was observed at 0° C. Additionally, with either metallation reagent, the in situ quench (Barbier) conditions did not work with a ketone as the electrophile.

PCT International Publication WO01/90072A1 describes the metallation of halo-heteroarylamine compounds using organomagnesium (Grignard) reagents. There, the lithiation of 2,5-dibromopyridine under cryogenic and high dilution conditions with the selectivity dependent on reaction time is taught to not be suitable for large scale synthesis.

The present invention describes an in situ quench protocol wherein n-butyllithium is added to a preformed mixture of a dihaloarene and ketone, including enolizable ketones, under both batch and flow conditions to selectively form a mono-substituted haloarene at non-cryogenic temperatures and relatively high concentrations of substrate.

The substituted haloarenes produced by the process of the present invention are useful intermediates in the preparation of N-aryl or N-heteroaryl substituted pharmaceutically active compounds that include selective antagonists, inverse agonists and partial agonists of serotonin 1 (5-HT$_1$) receptors useful in treating or preventing depression, anxiety, obsessive compulsive disorder (OCD) and other disorders for which a 5-HT$_1$ agonist or antagonist is indicated.

SUMMARY OF THE INVENTION

The present invention relates to a process of preparing a compound of the formula I having the structure:

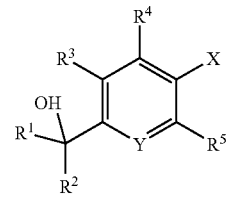

wherein $R^1$ and $R^2$ are independently selected from the group consisting of hydrogen, $(C_1-C_8)$alkyl, $(C_1-C_8)$alkoxy-$(C_1-C_8)$alkyl-, $(C_3-C_8)$cycloalkyl-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein $R^1$ and $R^2$ together with the carbon to which they are attached form a 4 to 8 membered cycloalkyl ring, wherein said cycloalkyl ring may be optionally substituted with one to three substituents selected from the group consisting of $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, and heteroaryl$(C_1-C_8)$alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is a halogen with atomic number less than or equal to the selected Z, as defined below; wherein Y is N;

comprising: (a) forming a mixture of a compound of the formula II having the structure:

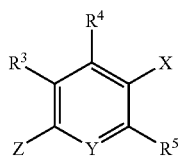

wherein Z is either bromo or iodo; and, X, Y, R³, R⁴, and R⁵ are as defined above;

with a compound of the formula III having the structure:

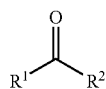

wherein R¹ and R² are as defined above preferably, in a non-coordinating solvent such as toluene;

(b) treating the mixture formed in step (a) with a (C₁–C₈) alkyl lithium compound; and, (c) quenching the mixture formed in (b) with a proton donor so as to form the compound of formula I.

In another aspect, the present invention relates to a continuous flow process of preparing a compound of the formula I having the structure:

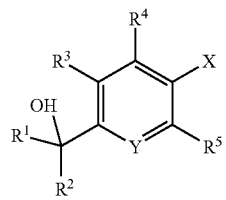

wherein R¹ and R² are independently selected from the group consisting of hydrogen, (C₁–C₈)alkyl, (C₁–C₈)alkoxy-(C₁–C₈)alkyl-, (C₃–C₈)cycloalkyl-, (C₁–C₈)alkoxy-(C₄–C₈)cycloalkyl-, aryl, aryl(C₁–C₈)alkyl, heteroaryl, heteroaryl(C₁–C₈)alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein R¹ and R² together with the carbon to which they are attached form a 4 to 8 membered cycloalkyl ring, wherein said cycloalkyl ring may be optionally substituted with one to three substituents selected from the group consisting of (C₁–C₈)alkyl, (C₁–C₈)alkoxy, (C₁–C₈)alkoxy-(C₁–C₈)alkyl-, (C₄–C₈)cycloalkyl-, (C₄–C₈)cycloalkoxy-, (C₁–C₈)alkoxy-(C₄–C₈)cycloalkyl-, aryl, aryl(C₁–C₈)alkyl, heteroaryl, heteroaryl(C₁–C₈)alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein R³, R⁴, and R⁵ are independently selected from the group consisting of hydrogen, (C₁–C₈)alkyl, (C₁–C₈)alkoxy, (C₁–C₈)alkoxy-(C₁–C₈)alkyl-, (C₄–C₈)cycloalkyl-, (C₄–C₈)cycloalkoxy-, (C₁–C₈)alkoxy-(C₄–C₈)cycloalkyl-, aryl, aryl(C₁–C₈)alkyl, heteroaryl, and heteroaryl(C₁–C₈)alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is a halogen with atomic number less than or equal to the selected Z, as defined below;

wherein Y is N;

comprising (a) forming a mixture of a compound of the formula II

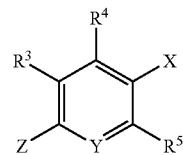

wherein Z is either bromo or iodo; and, X, Y, R³, R⁴, and R⁵ are as defined above, with a compound of the formula III:

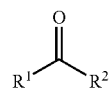

wherein R¹ and R² are as defined above;

wherein said mixture, preferably in a non-coordinating solvent such as toluene, forms a first reagent stream;

(b) forming a second reagent stream comprising a (C₁–C₈)alkyl lithium compound;

(c) combining the first reagent stream with the second reagent stream in a mixing zone; and, (d) quenching the mixture formed in (c) with a proton donor so as to form the compound of formula I.

The process of the present invention also relates to a process of preparing a compound of the formula IV having the structure:

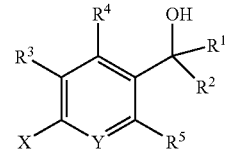

wherein R¹ and R² are independently selected from the group consisting of hydrogen, (C₁–C₈)alkyl, (C₁–C₈)alkoxy-(C₁–C₈)alkyl-, (C₃–C₈)cycloalkyl-, (C₁–C₈)alkoxy-(C₄–C₈)cycloalkyl-, aryl, aryl(C₁–C₈)alkyl, heteroaryl, heteroaryl(C₁–C₈)alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein R¹ and R² together with the carbon to which they are attached form a 4 to 8 membered cycloalkyl ring, wherein said cycloalkyl ring may be optionally substituted with one to three substituents selected from the group consisting of (C₁–C₈)alkyl, (C₁–C₈)alkoxy, (C₁–C₈)alkoxy-(C₁–C₈)alkyl-, (C₄–C₈)cycloalkyl-, (C₄–C₈)cycloalkoxy-, (C₁–C₈)alkoxy-(C₄–C₈)cycloalkyl-, aryl, aryl(C₁–C₈)alkyl, heteroaryl, heteroaryl($C_1$–$C_8$)alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, ($C_1$–$C_8$)alkyl, ($C_1$–$C_8$)alkoxy, ($C_1$–$C_8$)alkoxy-($C_1$–$C_8$)alkyl-, ($C_4$–$C_8$)cycloalkyl-, ($C_4$–$C_8$)cycloalkoxy-, ($C_1$–$C_8$)alkoxy-($C_4$–$C_8$)cycloalkyl-, aryl, aryl($C_1$–$C_8$)alkyl, heteroaryl, and heteroaryl($C_1$–$C_8$)alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is a halogen with atomic number less than or equal to the selected Z, as defined below;

wherein Y is N or C;

comprising: (a) forming a mixture of a compound of the formula V having the structure:

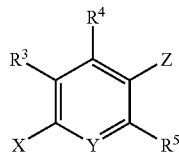

wherein Z is either bromo or iodo; and, X, Y, $R^3$, $R^4$, and $R^5$ are as defined above;

with a compound of the formula III having the structure:

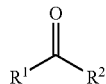

wherein $R^1$ and $R^2$ are as defined above;

in a coordinating solvent such as tetrahydrofuran, or a hydrocarbon solvent mixture thereof;

(b) treating the mixture formed in step (a) with a ($C_1$–$C_8$) alkyl lithium compound; and, (c) quenching the mixture formed in (b) with a proton donor so as to form the compound of formula IV.

The process of the present invention also relates to a continuous flow process of preparing a compound of the formula IV having the structure:

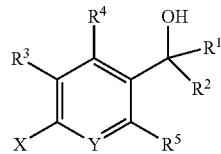

wherein $R^1$ and $R^2$ are independently selected from the group consisting of hydrogen, ($C_1$–$C_8$)alkyl, ($C_1$–$C_8$)alkoxy-($C_1$–$C_8$)alkyl-, ($C_4$–$C_8$)cycloalkyl-, ($C_1$–$C_8$)alkoxy-($C_4$–$C_8$)cycloalkyl-, aryl, aryl($C_1$–$C_8$)alkyl, heteroaryl, heteroaryl($C_1$–$C_8$)alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein $R^1$ and $R^2$ together with the carbon to which they are attached form a 4 to 8 membered cycloalkyl ring, wherein said cycloalkyl ring may be optionally substituted with one to three substituents selected from the group consisting of ($C_1$–$C_8$)alkyl, ($C_1$–$C_8$)alkoxy, ($C_1$–$C_8$)alkoxy-($C_1$–$C_8$)alkyl-, ($C_4$–$C_8$)cycloalkyl-, ($C_4$–$C_8$)cycloalkoxy-, ($C_1$–$C_8$)alkoxy-($C_4$–$C_8$)cycloalkyl-, aryl, aryl($C_1$–$C_8$)alkyl, heteroaryl, heteroaryl($C_1$–$C_8$)alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, ($C_1$–$C_8$)alkyl, ($C_1$–$C_8$)alkoxy, ($C_1$–$C_8$)alkoxy-($C_1$–$C_8$)alkyl-, ($C_4$–$C_8$)cycloalkyl-, ($C_4$–$C_8$)cycloalkoxy-, ($C_1$–$C_8$)alkoxy-($C_4$–$C_8$)cycloalkyl-, aryl, aryl($C_1$–$C_8$)alkyl, heteroaryl, and heteroaryl($C_1$–$C_8$)alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is a halogen with atomic number less than or equal to the selected Z, as defined below;

wherein Y is N or C;

comprising (a) forming a mixture of a compound of the formula V having the structure:

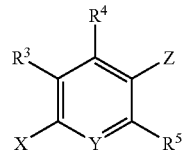

wherein Z is either bromo or iodo; and, X, Y, $R^3$, $R^4$, and $R^5$ are as defined above, with a compound of the formula III:

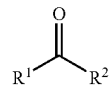

wherein $R^1$ and $R^2$ are as defined above;

wherein said mixture in a coordinating solvent such as tetrahydrofuran, or a hydrocarbon solvent mixture thereof forms a first reagent stream;

(b) forming a second reagent stream comprising a ($C_1$–$C_8$)alkyl lithium compound;

(c) combining the first reagent stream with the second reagent stream in a mixing zone; and, (d) quenching the mixture formed in (c) with a proton donor so as to form the compound of formula IV.

The process of the present invention also relates to a process wherein halogen-lithium interchange and in-situ quench of the newly formed lithium reagent with a carbonyl reactant are conducted at significantly higher temperatures and significantly higher concentrations than conventional processes, in which the lithiated arene is separately generated, usually at about −78° C. and a concentration of about 0.08 M due to solubility constraints, followed by treatment with the carbonyl reactant. In contrast to such conventional processes, the batch and flow process of the instant invention can be conducted at temperatures of about −10° C. to about 40° C.

The process of the present invention also relates to a process wherein halogen-lithium interchange and in-situ quench of the newly formed lithium reagent with a carbonyl reactant are conducted at significantly higher concentrations than conventional processes, in which the lithiated arene is separately generated, usually at a concentration of about 0.08 M due to solubility constraints, followed by treatment with the carbonyl reactant. In contrast to such conventional processes the batch and flow process of the instant invention can be conducted at concentrations of the compound of formula II, concentrations of the compound of formula III and concentrations of the ($C_1$–$C_8$)alkyl lithium compound of about 0.1 M to about 2.0 thereby resulting in an improvement in efficiency.

The process of the present invention also relates to a process to produce the compound of formula I or IV wherein a lithium reagent derived from the compound of formula II or V, respectively, is quenched in-situ with a compound of formula III having enolizable hydrogens.

The process of the present invention also relates to a process for selective mono-lithiation of a compound of the formula II or V wherein the halogen X or Z that is interchanged for lithium is determined by the solvent wherein the compound of formula II or V is treated with the ($C_1$–$C_8$) alkyl lithium compound.

The process of the present invention also relates to a process wherein competing side reactions such as addition of the ($C_1$–$C_8$)alkyl lithium compound to the compound of formula III, wherein $R^1$ and $R^2$ are as defined above, and dilithiation of the dihaloarene of formula II or V occur to only a minor extent.

DETAILED DESCRIPTION OF THE INVENTION

The process of the present invention for the preparation of the compound of formula I from the compound of formula II and the compound of formula III is illustrated and described in Schemes 1a and 1b and the following discussion, wherein $R^1$, $R^2$, $R^3$, $R^4$, $R^5$, X, Z, and Y are as defined above, unless otherwise indicated. Unless otherwise indicated reaction conditions include an inert atmosphere commonly used in the art such as nitrogen or argon.

Scheme 1

Scheme 1a - Non-coordinating Solvent

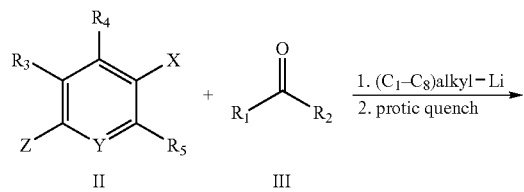

-continued

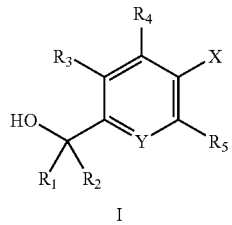

Scheme 1b - Coordinating Solvent

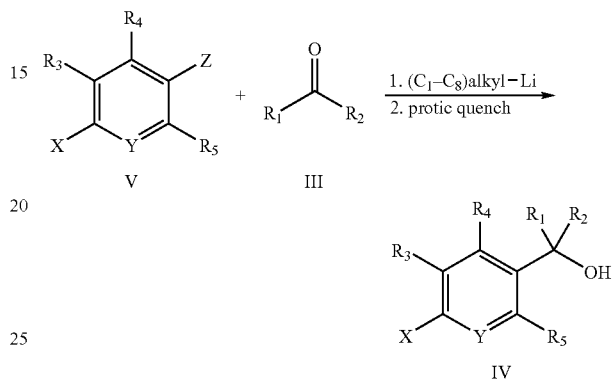

In Scheme 1a, a compound of formula I is prepared by (a) forming a mixture in a non-coordinating inert solvent, specifically toluene, of the dihaloarene of formula II wherein Y is N, Z is Br or I, and X is a halogen with an atomic number less than or equal to the selected Z, and the compound of formula III wherein $R^1$ and $R^2$ are as defined above, preferably wherein $R^1$ and $R^2$ are independently selected from ($C_1$–$C_8$)alkyl and ($C_3$–$C_8$)cycloalkyl-, or wherein $R^1$ and $R^2$ together with the carbon to which they are attached form a 4 to 8 membered cycloalkyl ring, wherein the concentration of the dihaloarene of formula II is about 0.1M to about 2.0M, preferably about 0.6M to about 0.8M, and the concentration of the compound of formula III is a multiple of about 0.9 times to about 1.1 times the concentration of the compound of formula II, preferably about 1 times the concentration of the compound of formula II and (b) treating said mixture at about −10° C. to about 40° C. with a solution of a ($C_1$–$C_8$)alkyl lithium compound, preferably n-butyl lithium, wherein the molar concentration of the alkyl lithium compound in the reaction mixture is a multiple of about 1 to about 1.2 times the concentration of the compound of formula II, preferably about 1 to about 1.1 times the concentration of the compound of formula II and (c) quenching with an alcohol such as methanol, ethanol or isopropanol, or methanol acidified with HCl.

A compound of formula I may also be prepared according to Scheme 1a by use of a continuous flow process wherein (a) a first reagent stream is formed in a non-coordinating inert solvent, preferably toluene, from a mixture of the dihaloarene of formula II, wherein Y is N, Z is Br or I, and X is a halogen with an atomic number less than or equal to the selected Z, and the compound of formula II, wherein $R^1$ and $R^2$ are as defined above, preferably wherein $R^1$ and $R^2$ are independently selected from ($C_1$–$C_8$)alkyl and ($C_3$–$C_8$) cycloalkyl-, or wherein $R^1$ and $R^2$ together with the carbon to which they are attached form a 4 to 8 membered cycloalkyl ring, wherein the concentration of the dihaloarene of formula II is about 0.1M to about 2.0M, preferably about 0.6M to about 0.8M and the concentration of the compound of formula III is a multiple of about 0.9 times to about 1.1 times the concentration of the compound of formula II, preferably about 1 times the concentration of the compound of formula II and (b) a second reagent stream is formed from a ($C_1$–$C_8$)alkyl lithium compound, preferably n-butyl lithium, wherein the molar concentration of said alkyl lithium compound after combining with the first reagent stream in subsequent step (c) is a multiple of about 1 to about 1.2 times the concentration of the compound of formula II, preferably about 1 to about 1.1 times the concentration of the compound of formula II in the first reagent stream and (c) combining the first reagent stream with the second reagent stream in a mixing zone at about –10° C. to about 40° C., preferably about 5° C. and (d) then treating the mixed streams with an alcohol such as methanol, ethanol or isopropanol, or methanol acidified with HCl.

In Scheme 1b, a compound of formula IV is prepared by (a) forming a mixture in a coordinating inert solvent, specifically tetrahydrofuran, of the dihaloarene of formula V wherein Y is N or C, Z is Br or I, and X is a halogen with an atomic number less than or equal to the selected Z, and the compound of formula III wherein $R^1$ and $R^2$ are as defined above, preferably wherein $R^1$ and $R^2$ are independently selected from ($C_1$–$C_8$)alkyl and ($C_3$–$C_8$)cycloalkyl-, or wherein $R^1$ and $R^2$ together with the carbon to which they are attached form a 4 to 8 membered cycloalkyl ring, wherein the concentration of the dihaloarene of formula II is about 0.1 M to about 2.0M, preferably about 0.6M to about 0.8M, and the concentration of the compound of formula III is a multiple of about 0.9 times to about 1.1 times the concentration of the compound of formula II, preferably about 1 times the concentration of the compound of formula II and (b) treating said mixture at about –10° C. to about 40° C. with a solution of a ($C_1$–$C_8$)alkyl lithium compound, preferably n-butyl lithium, wherein the molar concentration of the alkyl lithium compound in the reaction mixture is a multiple of about 1 to about 1.2 times the concentration of the compound of formula II, preferably about 1 to about 1.1 times the concentration of the compound of formula II and (c) treating with an alcohol such as methanol, ethanol or isopropanol, or methanol acidified with HCl.

A compound of formula IV may also be prepared according to Scheme 1b by use of a continuous flow process wherein (a) a first reagent stream is formed in a coordinating inert solvent, preferably tetrahydrofuran, from a mixture of the dihaloarene of formula V, wherein Y is N or C, Z is Br or I, and X is a halogen with an atomic number less than or equal to the selected Z, and the compound of formula III, wherein $R^1$ and $R^2$ are as defined above, preferably wherein $R^1$ and $R^2$ are independently selected from ($C_1$–$C_8$)alkyl and ($C_3$–$C_8$)cycloalkyl-, or wherein $R^1$ and $R^2$ together with the carbon to which they are attached form a 4 to 8 membered cycloalkyl ring, wherein the concentration of the dihaloarene of formula II is about 0.1M to about 2.0M, preferably about 0.6M to about 0.8M and the concentration of the compound of formula III is a multiple of about 0.9 times to about 1.1 times the concentration of the compound of formula II, preferably about 1 times the concentration of the compound of formula II and (b) a second reagent stream is formed from a ($C_1$–$C_8$)alkyl lithium compound, preferably n-butyl lithium, wherein the molar concentration of said alkyl lithium compound after combining with the first reagent stream in subsequent step (c) is a multiple of about 1 to about 1.2 times the concentration of the compound of formula II, preferably about 1 to about 1.1 times the concentration of the compound of formula I in the first reagent stream and (c) combining the first reagent stream with the second reagent stream in a mixing zone at about –10° C. to about 40° C., preferably about 10° C. and (d) then treating the mixed streams with an alcohol such as methanol, ethanol or isopropanol, or methanol acidified with HCl.

As will be evident to those skilled in the art, the concentrations of reactants within the first and second streams may be independently varied and the relative rate of flow of the streams may also be adjusted to produce in the mixing zone any desired ratio of the concentration of alkyl lithium compound to the concentrations of dihaloarene and carbonyl compound.

Unless otherwise indicated, the product distributions reported are uncorrected GC/MS ratios.

EXAMPLE 1

2-(3-hydroxy-pentane-3-yl)-5-bromo-pyridine—
(Batch Process)

A toluene solution (24 mL) containing 2,5-dibromopyridine (21.11 mmoles) and 3-pentanone (21.11 mmoles) were placed in a 125 mL jacketed flask under $N_2$ at 20° C. in an ice bath. n-BuLi in hexanes (17.2 mL, 1.3 M, 22.36 moles; 1.06 equiv) was added via a syringe pump delivering at 0.25 mL/min. The mixture was stirred for 5 min and then quenched with 30 mL of MeOH. The reaction mixture was diluted with EtOAc (10 □L in 1 mL EtOAc) and analyzed by GC/MS. The major product was 2-(3-hydroxy-pentane-3-yl)-5-bromo-pyridine (55.33%) indicating selective lithiation at the 2 position. The major product was isolated and purified by column chromatography to afford 33% isolated yield.

EXAMPLE 2

2-(3-hydroxy-pentane-3-yl)-5-bromo-pyridine—
(Flow Process)

2,5-Dibromopyridine (5.0 g; 0.021 moles) and 3-pentanone (2.24 mL; 0.021 moles) were dissolved in 24 mL of toluene to form a 0.75 M solution, as determined by the total solution volume. n-Butyllithium in hexanes from Aldrich was titrated three times with diphenylacetic acid in tetrahydrofuran and the average titration indicated a 1.43M concentration.

The reaction was run in a CPC Cytos flow system set at +5° C. The 1.43 M n-BuLi solution was used in Stream A and the 0.75 M 2,5-dibromopyridine, 0.75 M 3-pentanone solution was in Stream B. Stream A was set at a flow rate of 1.0 mL/min and Stream B was set at 1.8 mL/min to afford a reaction stream of 1.06 eq n-BuLi: 1.0 eq 2,5-dibromopyridine: 1.0 eq 3-pentanone. To ensure consistency in sampling, the system was allowed to flow for a minimum of 5–6 min before the reaction flow was collected. The reaction flow was collected for a total of 5 min and quenched into 10 mL of MeOH. A portion of the quenched reaction mixture was diluted with EtOAc (10 □L in 1 mL EtOAc) and analyzed by GC/MS. The major product was 2-(3-hydroxy-pentane-3-yl)-5-bromo-pyridine (58.1%) indicating selective lithiation at the 2 position. The complete product distribution is given in Table 1. The major product was isolated by column chromatography to afford a 34% isolated yield

EXAMPLE 3

Example 1 was repeated using tetrahydrofuran (THF) as the solvent and was run at 5° C. The major product was 2-bromo-5-(3-hydroxy-pentane-3-yl)-pyridine (68.8%) indicating selective lithiation at the 5 position. The product distribution is given in Table 1.

EXAMPLE 4

Example 2 was repeated using tetrahydrofuran (THF) as the solvent The flow rate of Stream A (n-BuLi) was 1.0 mL/min and for Stream B (2,5-dibromopyridine/3-pentanone/THF) the flow rate was 1.9 mL/min for a stream of 1.06 eq n-BuLi/1.0 eq 2,5-dibromopyridine and 1.0 eq 3-pentanone. The major product was 2-bromo-5-(3-hydroxy-pentane-3-yl)-pyridine (60.7%) indicating selective lithiation at the 5 position. The product distribution is given in Table 1.

EXAMPLE 6

The procedure of Example 3 was repeated using 1,4 dibromobenzene in place of 2,5-dibromopyridine. The major product was 4-(3-hydroxy-pentane-3-yl)-bromobenzene (57.3%) indicating selective mono-lithiation. The product distribution is given in Table 2.

EXAMPLE 7

The procedure of Example 4 was repeated using 1,4 dibromobenzene in place of 2,5-dibromopyridine. The temperature of the flow system was set at +10° C. The flow rate of Stream A (n-BuLi) was 1.0 mL/min and the flow rate of Stream B (1,4-dibromobenzene/3-pentanone/THF) was 1.9 mL/min to give a reaction stream of 1.02 eq n-BuLi/1.0 eq 1,4-dibromobenzene/1.0 eq 3-pentanone. The major product was 4-(3-hydroxy-pentane-3-yl)-bromobenzene (53.3%) indicating selective mono-lithiation. The product distribution is given in Table 2. The major product was isolated by column chromatography to afford a 35% isolated yield.

TABLE 1

|   | 3-bromo pyridine | 2-bromo-pyridine | 3-hydroxy-3-ethyl-heptane | 2,5-di-bromo-pyridine | 2-(3-hydroxy-pentane-3-yl)-5-bromo-pyridine | 2-bromo-5-(3-hydroxy-pentane-3-yl)-pyridine | 2,5-di(3-hydroxy-pentane-3-yl)-pyridine | 5,5'-dibromo-2,2'-dipyridyl |
|---|---|---|---|---|---|---|---|---|
| Example 1 (Batch, Toluene) | 7.0% | 0% | 10.1% | 0% | 76.7% | 3.9% | 0% | 2.3% |
| Example 2 (Flow, Toluene) | 5.3% | 0% | 10.5% | 15.9% | 58.1% | 6.5% | 3.8% | 0% |
| Example 3 (Batch, THF) | 0% | 8.7% | 3.9% | 0% | 11.2% | 68.8% | — | — |
| Example 4 (Flow, THF) | 0% | 2.8% | 4.8% | 12.0% | 1.9% | 60.7% | 2.4% | 0% |

EXAMPLE 5

The general procedure of Example 1 was repeated using 1,4 dibromobenzene in place of 2,5-dibromopyridine. About 1.4% of the desired product 4-(3-hydroxy-pentane-3-yl)-bromo-benzene was formed. The product distribution is given in Table 2.

TABLE 2

|   | Reaction Type | Solvent | bromo-benzene | 3-hydroxy-3-ethyl-heptane | 1,4 dibromo-benzene | 4-(3-hydroxy-pentane-3-yl)-bromo-benzene | 1,4-di(3-hydroxy-pentane-3-yl)-benzene |
|---|---|---|---|---|---|---|---|
| Example 5 | Batch | Toluene | 1.1% | 28.0% | 68.8% | 1.4% | — |
| Example 6 | Batch | THF | 15.4% | 6.4% | 2.8% | 57.3% | 1.7% |
| Example 7 | Flow | THF | 6.5% | 10.6% | 18.2% | 53.3% | 5.5% |

EXAMPLES 8–17

The general procedures of Examples 1–4 were followed in Examples 8–17 in which 2,5 dibromopyridine was lithiated and adducts formed with different enolizable ketones. However, the batch reactions in Examples 8–17 were not run in a jacketed flask and the BuLi was added quickly via a manual syringe, instead of a syringe pump. The solution was chilled in a 0° C. ice bath prior to addition. Product distribution was determined by GC/MS (uncorrected) as described above. The percent of 2 adduct reflects the extent of lithiation at the 2 position and the percent of 5 adduct reflects the percent of lithiation at the 5 position.

TABLE 3

| | Ketone | Reaction Type | Solvent | 2-Adduct (A) % | 5-Adduct (B) % | A:B |
|---|---|---|---|---|---|---|
| Example 8 | 2-methyl-3-pentanone | Batch | toluene | 75 | 2 | 47:1 |
| Example 9 | 2-methyl-3-pentanone | Flow | toluene | 60 | 8 | 8:1 |
| Example 10 | 3-methyl-2-butanone | Batch | toluene | 67 | 2 | 30:1 |
| Example 11 | 3-methyl-2-butanone | Flow | toluene | 65 | 4 | 18:1 |
| Example 12 | cyclopentanone | Batch | toluene | 33 | 2 | 22:1 |
| Example 13 | cyclopentanone | Flow | toluene | 34 | 3 | 10:1 |
| Example 14 | cyclopentanone | Flow | THF | 0 | 64 | 100% B |
| Example 15 | cyclohexanone | Batch | toluene | 54 | 3 | 20:1 |
| Example 16 | cyclohexanone | Flow | toluene | 52 | 3 | 14:1 |
| Example 17 | acetone | Batch | toluene | 34 | 3 | 11:1 |

EXAMPLE 18

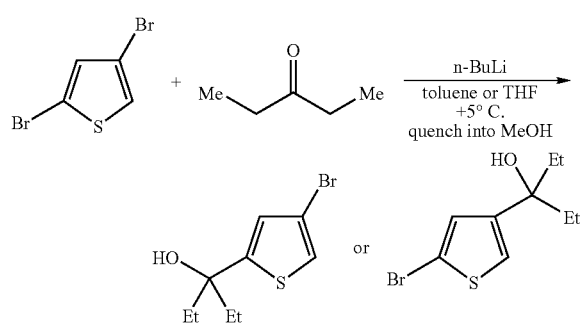

2,4-Dibromothiophene (2.02 g; moles) and 3-pentanone (0.88 mL; 0.070 moles) were dissolved in 11.1 mL of toluene or THF to afford a 0.6 M solution. n-BuLi in hexanes from Aldrich was titrated three times with diphenylacetic acid in tetrahydrofuran and the average titration indicated a 2.3 M concentration. The temperature of the CPC Cytos flow system was set to +5° C. The 2.3 M n-BuLi solution was used in Stream A and the 0.6 M 2,4-dibromothiophene solution was in Stream B. Stream A was set at a flow rate of 0.5 mL/min and Stream B was set at 1.9 mL/min to afford a reaction stream of 1.0 eq n-BuLi: 1.0 eq 2,5-dibromopyridine: 1.0 eq 3-pentanone. The reaction flow was collected into MeOH. A portion of the quenched reaction mixture was diluted with EtOAc, analyzed by GC/MS and afforded a product distribution of:

THF:

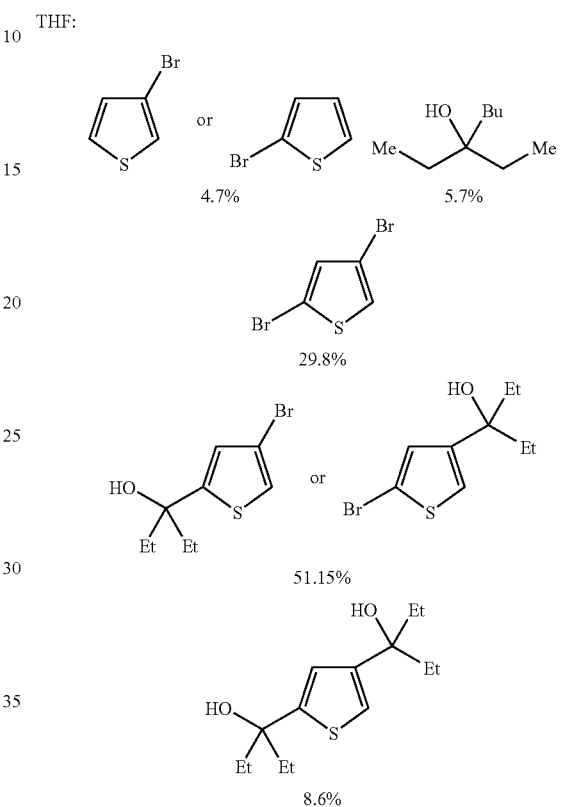

Toluene:

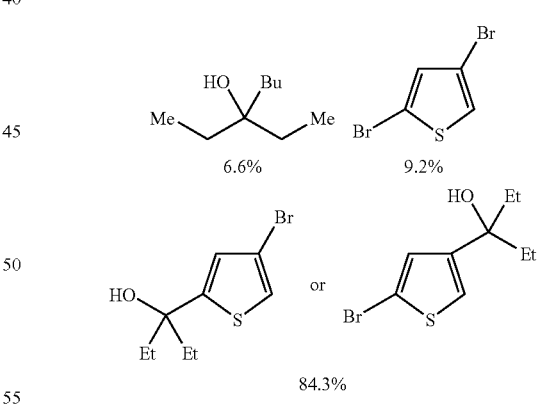

In both solvents, only one regioisomer is observed which is the same regardless of solvent. Regioselectivity dependence on solvent does not appear to play a role with 2,4-dibromothiophene.

What is claimed is:
1. A process of preparing a compound of the formula I having the structure:

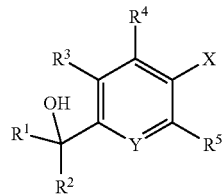

wherein $R^1$ and $R^2$ are independently selected from the group consisting of hydrogen, $(C_1-C_8)$alkyl, $(C_1-C_8)$alkoxy-$(C_1-C_8)$alkyl-, $(C_3-C_8)$cycloalkyl-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein $R^1$ and $R^2$ together with the carbon to which they are attached form a 4 to 8 membered cycloalkyl ring, wherein said cycloalkyl ring may be optionally substituted with one to three substituents selected from the group consisting of $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, and heteroaryl$(C_1-C_8)$alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is Br;

wherein Y is N;

comprising: (a) forming a mixture of a compound of the formula II having the structure:

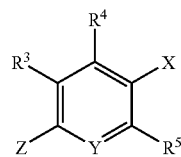

wherein Z is Br; and, X, Y, $R^3$, $R^4$, and $R^5$ are as defined above;

with a compound of the formula III having the structure:

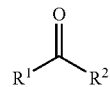

wherein $R^1$ and $R^2$ are as defined above in a non-coordinating reaction inert solvent, and wherein the compound of formula III contains enolizable hydrogens;

(b) treating the mixture formed in step (a) with a $(C_1-C_8)$ alkyl lithium compound at a temperature of about $-10°$ C. to about $40°$ C.; and, (c) quenching the mixture formed in (b) with a proton donor so as to form the compound of formula I.

2. The process of claim 1, wherein Y is N and $R^3$, $R^4$, and $R^5$ are hydrogen, and wherein X is Br and Z is Br.

3. The process of claim 1, wherein the reaction inert solvent is an aromatic hydrocarbon selected from the group consisting of toluene and xylenes.

4. The process of claim 1, wherein in step (a) the concentration of the compound of formula II is about 0.1 M to about 2.0M and the concentration of the compound of formula III is a multiple of about 0.9 times to about 1.1 times the concentration of the compound of formula II, and wherein in step (b) the concentration of the $(C_1-C_8)$alkyl lithium compound contained in the reaction inert solvent is a multiple of about 1 to about 1.2 times the aforesaid concentration of the compound of formula II.

5. The process of claim 1, wherein $R_1$ and $R_2$ are independently selected from $(C_1-C_8)$alkyl and $(C_3-C_8)$cycloalkyl-, or $R_1$ and $R_2$ together with the carbon to which they are attached form a 4 to 8 membered cycloalkyl ring.

6. A continuous flow process of preparing a compound of the formula I having the structure:

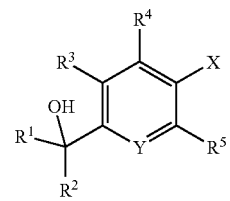

wherein $R^1$ and $R^2$ are independently selected from the group consisting of hydrogen, $(C_1-C_8)$alkyl, $(C_1-C_8)$alkoxy-$(C_1-C_8)$alkyl-, $(C_3-C_8)$cycloalkyl-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein $R^1$ and $R^2$ together with the carbon to which they are attached form a 4 to 8 membered cycloalkyl ring, wherein said cycloalkyl ring may be optionally substituted with one to three substituents selected from the group consisting of $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, and heteroaryl$(C_1-C_8)$alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is Br;

wherein Y is N;

comprising (a) forming a mixture of a compound of the formula II

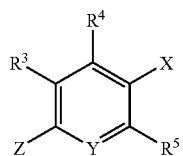

wherein Z is Br; and, X, Y, $R^3$, $R^4$, and $R^5$ are as defined above, with a compound of the formula III:

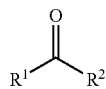

wherein $R^1$ and $R^2$ are as defined above, and wherein the compound of formula III contains enolizable hydrogens;

wherein said mixture in a non-coordinating reaction inert solvent forms a first reagent stream;

(b) forming a second reagent stream comprising a $(C_1-C_8)$alkyl lithium compound;

(c) combining the first reagent stream with the second reagent stream in a mixing zone at a temperature of about –10° C. to about 40° C.; and (d) quenching the mixture formed in (c) with a proton donor so as to form the compound of formula I.

7. The process of claim 6, wherein Y is N; $R^3$, $R^4$, and $R^5$ are hydrogen; and, X is Br and Z is Br.

8. The process of claim 6, wherein the reaction inert solvent is an aromatic hydrocarbon selected from the group consisting of toluene and xylenes.

9. The process of claim 6 wherein in the first reagent stream in step (a), the concentration of the compound of formula II is about 0.1 M to about 2.0M and the concentration of the compound of formula III is a multiple of about 0.9 times to about 1.1 times the concentration of the compound of formula II, and wherein the flow rates are set such that in step (c), the concentration of the $(C_1-C_8)$alkyl lithium compound contained in the reaction inert solvent is a multiple of about 1 to about 1.2 times the aforesaid concentration of the compound of formula II.

10. The process of claim 6, wherein $R^1$ and $R^2$ are independently selected from $(C_1-C_8)$alkyl and $(C_3-C_8)$cycloalkyl-, or $R^1$ and $R^2$ together with the carbon to which they are attached form a 4 to 8 membered cycloalkyl ring.

11. A process of preparing a compound of the formula IV having the structure:

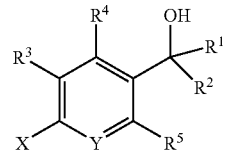

wherein $R^1$ and $R^2$ are independently selected from the group consisting of hydrogen, $(C_1-C_8)$alkyl, $(C_1-C_8)$alkoxy-$(C_1-C_8)$alkyl-, $(C_3-C_8)$cycloalkyl-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein $R^1$ and $R^2$ together with the carbon to which they are attached form a 4 to 8 membered cycloalkyl ring, wherein said cycloalkyl ring may be optionally substituted with one to three substituents selected from the group consisting of $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, and heteroaryl$(C_1-C_8)$alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is Br;

wherein Y is N or C;

comprising: (a) forming a mixture of a compound of the formula V having the structure:

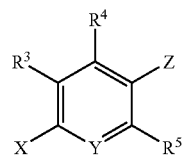

wherein Z is bromo; and, X, Y, $R^3$, $R^4$, and $R^5$ are as defined above;

with a compound of the formula III having the structure:

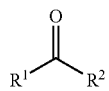

wherein $R^1$ and $R^2$ are as defined above, and wherein the compound of formula III contains enolizable hydrogens;

in coordinating reaction inert solvent;

(b) treating the mixture formed in step (a) with a $(C_1-C_8)$ alkyl lithium compound at a temperature of about −10° C. to about 40° C.; and, (c) quenching the mixture formed in (b) with a proton donor so as to form the compound of formula IV.

12. The process of claim 11, wherein Y is N or C and $R^3$, $R^4$, and $R^5$ are H; and wherein X is Br and Z is Br.

13. The process of claim 11, wherein the reaction inert solvent is selected from the group consisting of tetrahydrofuran and a hydrocarbon solvent mixture thereof.

14. The process of claim 11, wherein in step (a) the concentration of the compound of formula V is about 0.1M to about 2.0M and the concentration of the compound of formula III is a multiple of about 0.9 times to about 1.1 times the concentration of the compound of formula V, and wherein in step (b) the concentration of the $(C_1-C_8)$alkyl lithium compound contained in the reaction inert solvent is a multiple of about 1 to about 1.2 times the aforesaid concentration of the compound of formula V.

15. The process of claim 11, wherein $R^1$ and $R^2$ are independently selected from $(C_1-C_8)$alkyl and $(C_3-C_8)$cycloalkyl-, or $R^1$ and $R^2$ together with the carbon to which they are attached form a 4 to 8 membered cycloalkyl ring.

16. A continuous flow process of preparing a compound of the formula IV having the structure:

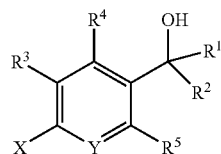

wherein $R^1$ and $R^2$ are independently selected from the group consisting of hydrogen, $(C_1-C_8)$alkyl, $(C_1-C_8)$alkoxy-$(C_1-C_8)$alkyl-, $(C_3-C_8)$cycloalkyl-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms; or, wherein $R^1$ and $R^2$ together with the carbon to which they are attached form a 4 to 8 membered cycloalkyl ring, wherein said cycloalkyl ring may be optionally substituted with one to three substituents selected from the group consisting of $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, heteroaryl$(C_1-C_8)$alkyl, wherein aryl is phenyl or naphthyl, and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein $R^3$, $R^4$, and $R^5$ are independently selected from the group consisting of hydrogen, $(C_1-C_8)$alkyl, $(C_1-C_8)$alkoxy, $(C_1-C_8)$alkoxy-$(C_1-C_8)$alkyl-, $(C_4-C_8)$cycloalkyl-, $(C_4-C_8)$cycloalkoxy-, $(C_1-C_8)$alkoxy-$(C_4-C_8)$cycloalkyl-, aryl, aryl$(C_1-C_8)$alkyl, heteroaryl, and heteroaryl$(C_1-C_8)$alkyl, wherein aryl is phenyl or naphthyl and heteroaryl is a 5 to 7 membered heteroaryl ring containing from one to four heteroatoms in the ring selected from oxygen, nitrogen and sulfur, with the proviso that said ring cannot contain two adjacent oxygen atoms or two adjacent sulfur atoms;

wherein X is Br;

wherein Y is N or C;

comprising (a) forming a mixture of a compound of the formula V having the structure:

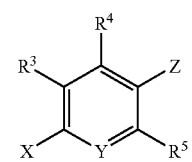

wherein Z is bromo; and, X, Y, $R^3$, $R^4$, and $R^5$ are as defined above, with a compound of the formula III:

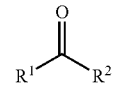

wherein $R^1$ and $R^2$ are as defined above, wherein the compound of formula III contains enolizable hydrogens;

in coordinating reaction inert solvent, wherein said mixture forms a first reagent stream;

(b) forming a second reagent stream comprising a $(C_1-C_8)$alkyl lithium compound;

(c) combining the first reagent stream with the second reagent stream in a mixing zone at a temperature of about −10° C. to about 40° C.; and, (d) quenching the mixture formed in (c) with a proton donor so as to form the compound of formula IV.

17. The process of claim 16, wherein Y is N or C; wherein $R^3$, $R^4$, and $R^5$ are H; and, wherein X is Br and Z is Br.

18. The process of claim 16, wherein the reaction inert solvent is selected from the group consisting of tetrahydrofuran and a hydrocarbon solvent mixture thereof.

19. The process of claim 16, wherein in the first reagent stream in step (a), the concentration of the compound of formula V is about 0.1 M to about 2.0M and the concentration of the compound of formula III is a multiple of about 0.9 times to about 1.1 times the concentration of the compound of formula V, and wherein the flow rates are set such that in step (c), the concentration of the $(C_1-C_8)$alkyl lithium compound contained in the reaction inert solvent is a multiple of about 1 to about 1.2 times the aforesaid concentration of the compound of formula V.

20. The process of claim 16, wherein $R^1$ and $R^2$ are independently selected from $(C_1-C_8)$alkyl and $(C_3-C_8)$cycloalkyl-, or $R_1$ and $R_2$ together with the carbon to which they are attached form a 4 to 8 membered cycloalkyl ring.

* * * * *